United States Patent [19]

Yamaguchi et al.

[11] Patent Number: 5,180,652
[45] Date of Patent: * Jan. 19, 1993

[54] LIGHT- AND HEAT-SENSITIVE COMPOSITION, AND RECORDING MATERIAL

[75] Inventors: Jun Yamaguchi; Sadao Ishige, both of Shizuoka; Kozo Sato, Kanagawa; Shintaro Washizu, Shizuoka; Isamu Itoh, Kanagawa, all of Japan

[73] Assignee: Fuji Photo Film Co., Ltd., Kanagawa, Japan

[ * ] Notice: The portion of the term of this patent subsequent to Jan. 1, 2008 has been disclaimed.

[21] Appl. No.: 466,906

[22] Filed: Jan. 18, 1990

[30] Foreign Application Priority Data

Jan. 18, 1989 [JP] Japan .................................. 1-9509
Dec. 4, 1989 [JP] Japan ................................ 1-314975

[51] Int. Cl.⁵ ..................... G03F 7/031; G03F 7/033; G03C 1/72; B41M 5/18

[52] U.S. Cl. ................... 430/281; 430/138; 430/280; 430/283; 430/285; 430/288; 430/330; 430/336; 430/339; 430/343; 430/915; 430/964; 503/202

[58] Field of Search ............... 430/336, 915, 288, 281, 430/284, 339, 330, 292, 138, 283, 285, 343, 964; 503/202

[56] References Cited

U.S. PATENT DOCUMENTS

| | | | |
|---|---|---|---|
| 4,529,681 | 7/1985 | Usami et al. | 430/138 |
| 4,632,899 | 12/1986 | Takeda | 430/281 |
| 4,894,358 | 1/1990 | Filosa et al. | 503/201 |
| 4,981,833 | 1/1991 | Sato | 503/202 |

Primary Examiner—Charles L. Bowers, Jr.
Assistant Examiner—John S. Y. Chu
Attorney, Agent, or Firm—Sughrue, Mion, Zinn, Macpeak & Seas

[57] ABSTRACT

A light- and heat-sensitive composition which contains a photo-hardenable composition and at least one dye, a light- and heat-sensitive recording material which contains a support having the composition provided on at least one side thereof, and an image-forming process using the recording material are disclosed.

11 Claims, No Drawings

LIGHT- AND HEAT-SENSITIVE COMPOSITION, AND RECORDING MATERIAL

FIELD OF THE INVENTION

The present invention relates to a novel light- and heat-sensitive composition based on photothermography for use in copiers, facsimile equipment, printers, labels, color proofs, overhead projectors, second original drawings, etc. The present invention also relates to a novel recording material and an image-forming process using the same.

More particularly, it relates to a novel light- and heat-sensitive composition which utilizes a photo-hardened reaction and a color-losing reaction of a dye caused by heating and which responds to visible light. Further, it relates to a recording material containing the composition and adapted for monosheet type use not requiring extra expendables, and to an image-forming process using the same.

BACKGROUND OF THE INVENTION

A process for obtaining an image by imagewise exposure and subsequent uniform heating for development is called photothermography (light- and heat-sensitive image-forming process), and is characterized in that it enables one to obtain an image with ease by a dry process.

Among such processes, there is known a process of forming a visible image by thermal development using a photo-polymerizable composition and a heat-sensitive color-forming material as disclosed in JP-A-52-89915 (The term "JP-A" as used herein means an "unexamined published Japanese patent application"). This process comprises using a recording material in which two components of a two-component type heat-sensitive color-forming material are separately provided inside and outside, or on both sides, of the photo-polymerizing composition, and exposing and heating the recording material to set the exposed portion where no color is formed since the thermal components do not migrate, with the coloration reaction taking place in unexposed portion where the thermal components migrate to cause the coloration reaction, thereby forming an image.

As another process, there is known a process of using a recording material which comprises a photopolymerizable composition composed of a vinyl monomer having an acidic group and a photo-polymerization initiator and a dye precursor capable of forming a dye with the aid of an acid, as is disclosed in JP A 61 123838. This recording material is designed to provide a visible image by imagewise exposure and subsequent uniform heating in the vicinity of the above-described dye precursor thereby to react the dye precursor with the non-polymerized and diffused monomer having an acidic group.

These recording materials permit recording with either ultraviolet rays or visible light (e.g., visible light laser or LED) depending upon their design.

In a recording process using ultraviolet rays and those recording materials, either a transfer type recording material using two sheets or a monosheet type recording material (which does not require an additional sheet and is therefore more preferable) may be employed. However, a monosheet type recording materials capable of being recorded by visible light cannot be obtained.

This is true because recording by visible light requires a colored spectrally sensitizing agent for absorbing visible light and initiating photo-polymerization which remains in monosheet type recording materials and makes the resulting image indistinct.

SUMMARY OF THE INVENTION

An object of the present invention is to provide a material capable of converting (i.e., developing) a polymer image obtained by photo hardened to a visible image by thermal processing, and an image-forming process using that material.

Another object of the present invention is to provide a recording material capable of responding to visible light and an image-forming process using that recording material.

A further object of the present invention is to provide a mono sheet type recording material requiring no unnecessary expendables.

These and other objects of the present invention will become apparent from the following description.

The above-described and other objects of the present invention are attained by a light- and heat-sensitive composition containing (a) a photo-hardenable composition and (b) a dye capable of losing its color upon being heated, a recording material containing that light- and heat-sensitive composition, and an image-forming process using that recording material.

DETAILED DESCRIPTION OF THE INVENTION

The term "photo-hardenable composition" as used herein means a photo-hardenable composition selected from among the group consisting of a photo-polymerizable composition comprising an ethylenically unsaturated compound and a photo polymerization initiator, a composition containing a photo-crosslinkable resin, and a mixture thereof.

According to the present invention, an image is obtained by a method comprising imagewise exposing a photo-hardenable composition containing a dye capable of losing its color upon heating, which may be utilized as a spectrally sensitizing dye, to set the composition, and then uniformly heating it to cause the dye to lose its color in the non-set portions, or a method comprising imagewise heating the photo-hardened composition containing the dye to cause the dye to lose its color, and then exposing to set the unheated portions.

In the photo-set portions, the thermal decomposition reaction of the dye is so slow that the dye does not lose its color, so that an image is formed.

In the present invention, a spectrally sensitizing dye in the unexposed portions loses its color, whereas the dye in photo-set portions maintains its color to form an image. Hence, a mono-sheet type light-sensitive material, which is difficult to obtain with the conventional process of allowing spectrally sensitizing dyes not to maintain their color, can be obtained by the present invention.

The recording materials of the present invention may be prepared in various forms depending upon the end use.

One preferable form is one wherein a layer comprising a photo-hardenable composition, a spectrally sensitizing dye and a binder is provided on a support.

Another preferable form is one wherein fine droplets, containing a light- and heat-sensitive composition comprising a photo-hardenable composition and a spectrally sensitizing dye, are provided on a support. In this case, the droplets may be the core substance within microcapsules.

The recording material of the present invention may be either a monocolor (a so-called B/W type recording material) or a full-color recording material. With full-color recording materials, there may be employed, for example, a form of multi-layer recording material wherein each layer contains a dye with a different hue and an associated photo-hardenable composition responding to light of different wavelengths. There may also be employed a form wherein a mixture of several kinds of microcapsules each retaining a dye with a different hue and an associated photo-hardenable composition responding to light of different wavelength is provided on a support.

As the photo-hardenable composition to be employed in the present invention, various compositions known in the art may be used, for instance, those shown in Kosar; *Light-sensitive Systems* (1965, John Wiley & Sons, Inc.), 2nd chapter, 3rd chapter, 4th chapter and 5th chapter, and The Photographic Society of Japan; *Basis of Photo-engineering; Non-silver Salt Photography*, pp. 133–56 (1982).

Examples of the photo-crosslinkable resin include, for example, polyvinyl cinnamate, polyvinyl cinnamylideneacetate, and a light-sensitive resin having α-phenylmaleimido group.

The present invention is hereinafter described by reference to a form, wherein a layer comprising an ethylenically unsaturated compound, a photo-polymerization initiator, a spectrally sensitizing dye which loses its color upon being heated, and a binder, is provided on a support. However, the present invention is not limited to this form.

The dyes which lose their colors upon being heated and which can be used in the present invention are those dyes represented by the following general formulae (I) to (IV):

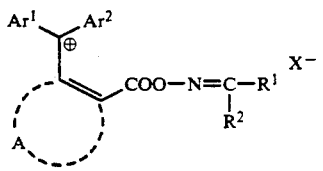
(I)

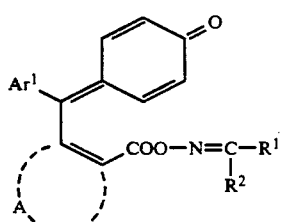
(II)

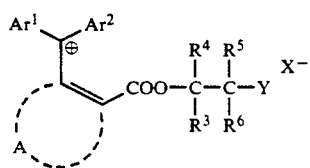
(III)

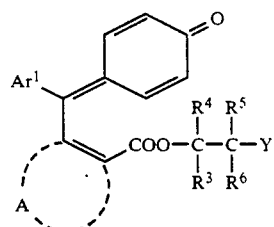
(IV)

wherein $AR^1$ and $Ar^2$ each represents an aryl group or a heteroaryl group and may be bound to each other to form a ring; $Rs^{1-6}$ each represents a hydrogen atom, an alkyl group, an alkenyl group, an aralkyl group, an aryl group or a heteroaryl group, provided that both $R^1$ and $R^2$ are not hydrogen atoms at the same time; Y represents CN, $NO_2$, $SO_2$-$R^7$, $SO$-$R^7$, $CO$-$R^7$, $COO$-$R^7$ or

in which $R^7$ and $R^8$ is each a hydrogen atom, an alkyl group, an alkenyl group, an aralkyl group, an aryl group or a heteroaryl group; A represents atoms necessary for forming a 5- or 6-membered ring; , $X^-$ represents a residue having an electric charge of -1, with the ring

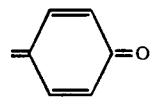

in the general formulae (II) and (IV) being optionally fused with an aromatic ring or a heterocyclic ring, and $Ar^1$, $Ar^2$, $R^1$, $R^2$, ring A and ring

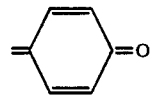

being optionally substituted by other substituents.

The general formulae (I) to (IV) are described in detail below.

In the above general formulae, $Ar^1$ and $Ar^2$ each represents an aryl group or a heteroaryl group, with those which possess an electron donative group (e.g., a dialkylamino group or an alkoxy group) in an o- or p-position being preferable. Particularly preferable examples thereof include a p-dialkylaminophenyl group, an o-alkoxy-p-dialkylaminophenyl group, and a 1,2-dialkyl-3-indolyl group. In addition, those wherein $Ar^1$ and $Ar^2$ are bound to each other via an oxygen atom to form a xanthene ring are also preferably used.

$R^1$ and $R^2$ each represents a hydrogen atom, an alkyl group, an alkenyl group, an aralkyl group, an aryl group or a heteroaryl group, with an aryl group and a heteroaryl group being preferable. Particularly preferable examples thereof include a hydrogen atom a p-dialkylaminophenyl group, o-alkoxy p-dialkylaminophenyl group, a 2,4,6-trialkoxyphenyl group, a 2,4,6-trialkyl phenyl group, a 1-naphthyl group, a 2-alkoxy-1-naphthyl group, a 2,4-dialkoxy-1-naphthyl group, a 1,2-dialkyl-3-indolyl group, etc.

Rs$^{3-6}$ each represents a hydrogen atom, an alkyl group, an alkenyl group, an aralkyl group, an aryl group or a heteroaryl group, with a hydrogen atom and groups having 1 to 5 carbon atoms being preferable.

Y represents CN, NO$_2$, SO$_2$-R$^7$, SO-R$^7$, CO-R$^7$, COO-R$^7$ or

in which R$^7$ and R$^8$ is each a hydrogen atom, an alkyl group, an alkenyl group, an aralkyl group, an aryl group or a heteroaryl group, with a hydrogen atom and groups having 1 to 5 carbon atoms being preferable. Y preferably includes SO$_2$CH$_3$, CN and COCH$_3$.

A represents atoms (e.g., C, N, O, etc.) necessary for forming a 5- or 6-membered ring. Specific examples thereof include a benzene ring, a naphthalene ring, an indole ring, a benzofuran ring, a benzothiophene ring, a pyridine ring, a pyrazine ring, a pyridazine ring, a pyrimidine ring and a quinoxaline ring. Of these, a benzene ring and a pyridine ring are particularly preferable.

X$^-$ represents a residue having an electric charge of $-1$, and preferable examples thereof include Cl$^-$, Br$^-$, I$^-$, BF$_4^-$, ZnCl$_3^-$, ClO$_4^-$, PF$_6^-$, HSO$_4^-$, TsO$^-$, and CF$_3$SO$_3^-$.

As a ring to be optionally fused with the ring of

in the general formulae (II) and (IV) there are, for example, a benzene ring, a naphthalene ring, an indole ring, a benzofuran ring, a benzothiophene ring, a pyridine ring, a pyrazine ring and a quinoxaline ring. Of these, a benzene ring and a pyridine ring are particularly preferable.

As a substituent on the ring of

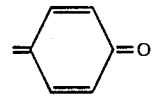

in the general formulae (II) and (IV), almost all ordinary substituents may be used, and one is selected depending upon the hue of the dye. For example, there are a halogen atom, a hydroxy group, a cyano group, a carboxy group, a sulfo group, an alkyl group, a cycloalkyl group, an aralkyl group, an aryl group, a heterocyclic group, an alkoxy group, an aryloxy group, an amino group, an acylamino group, a sulfonylamino group, an acyl group, a sulfonyl group, a carbamoyl group, a sulfamoyl group, an ureido group, a urethane group, an alkylthio group, an arylthio group, a nitro group and an alkoxycarbonyl group. Two or more of these substituents may exist. In this case, the substituents may be the same or different. Preferable examples thereof include benzologues.

As a substituent on the ring A, there are the same substituents as mentioned above.

Specific nonlimiting examples of the dyes to be used in the present invention are illustrated below.

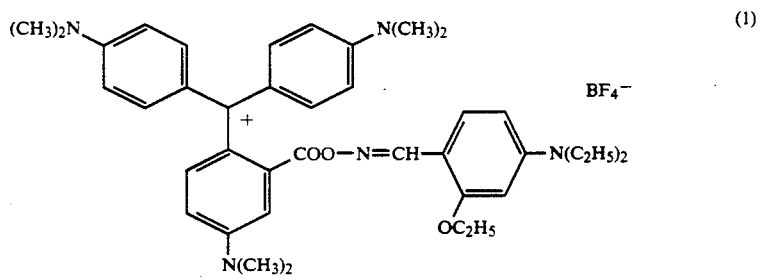

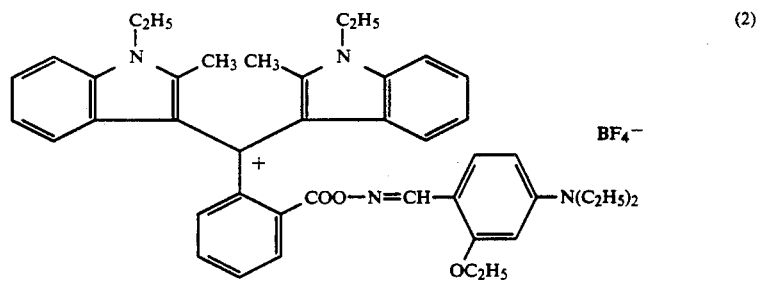

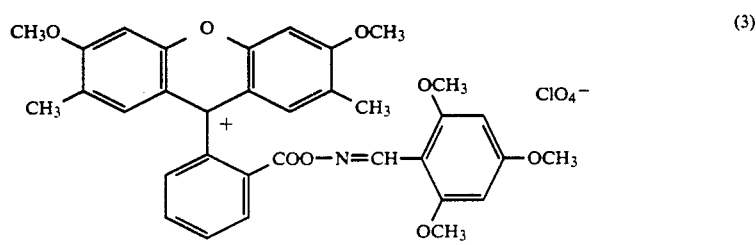

-continued
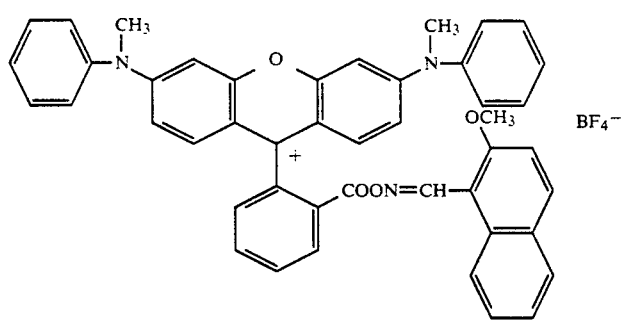
(4)
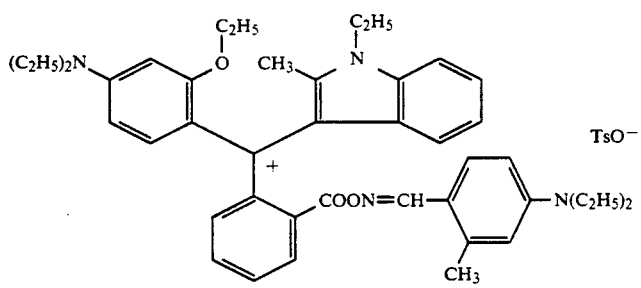
(5)
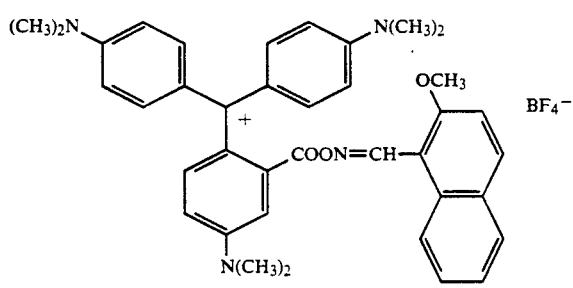
(6)
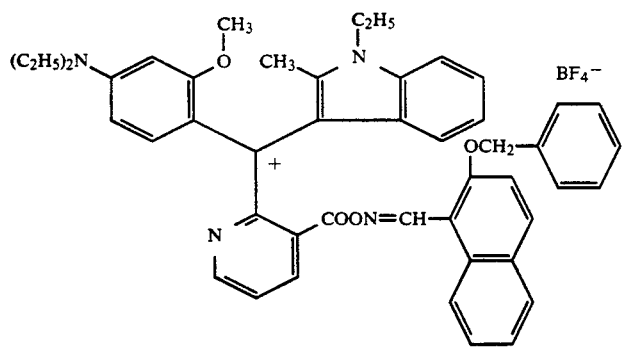
(7)
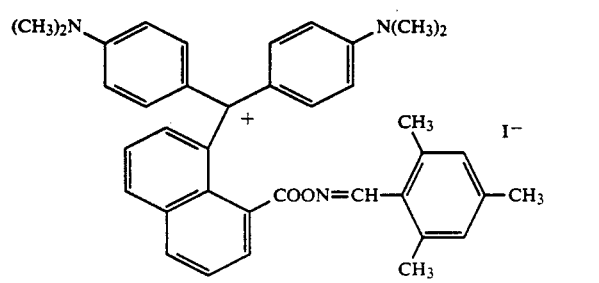
(8)

-continued
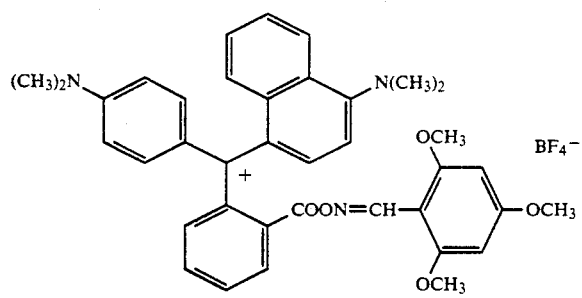
(9)
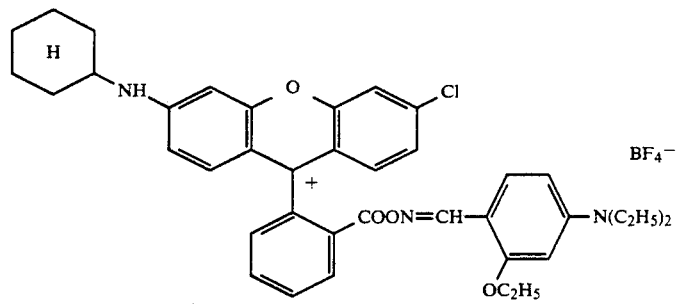
(10)
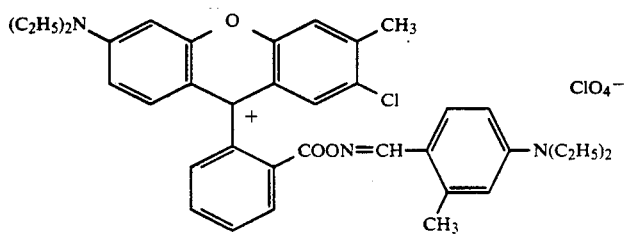
(11)
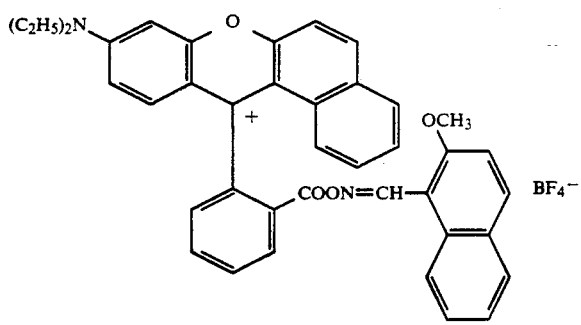
(12)
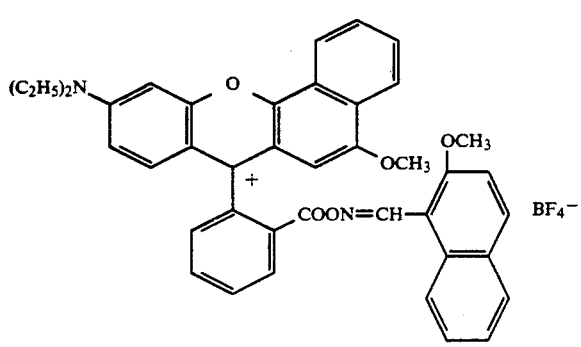
(13)

-continued
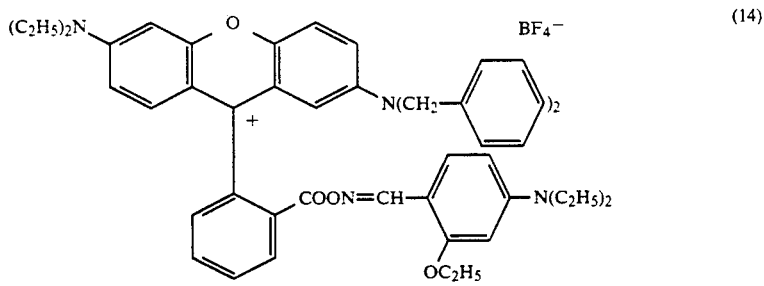
(14)
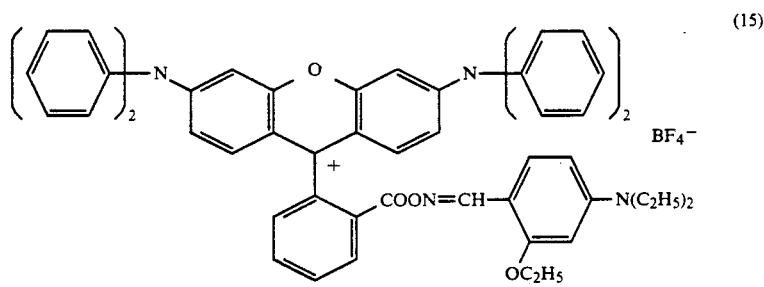
(15)
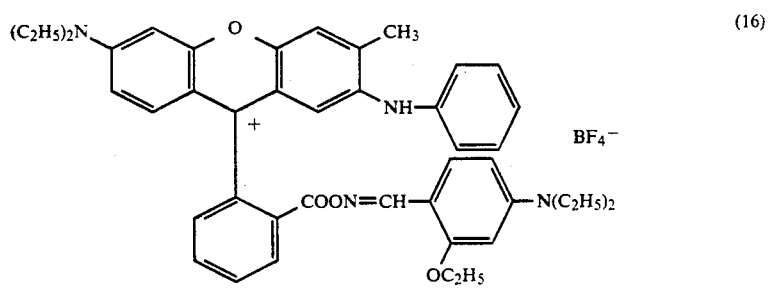
(16)
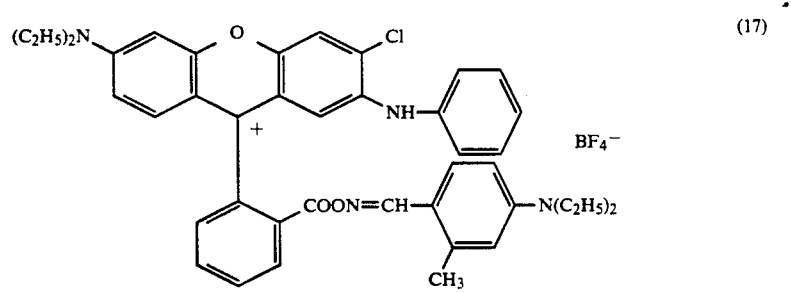
(17)
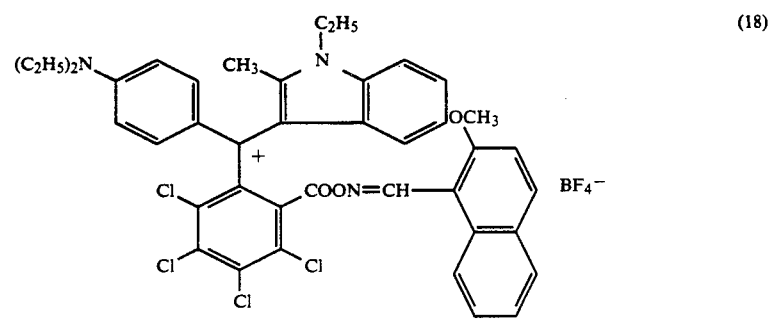
(18)

-continued
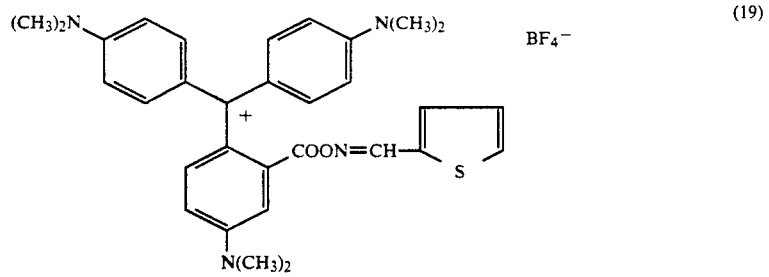
(19)
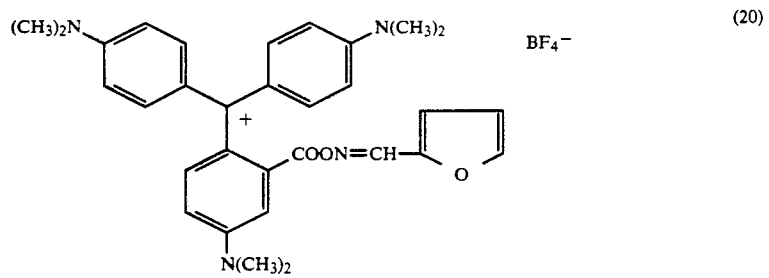
(20)
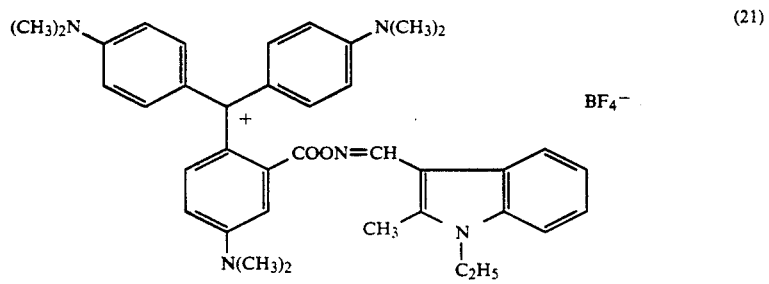
(21)
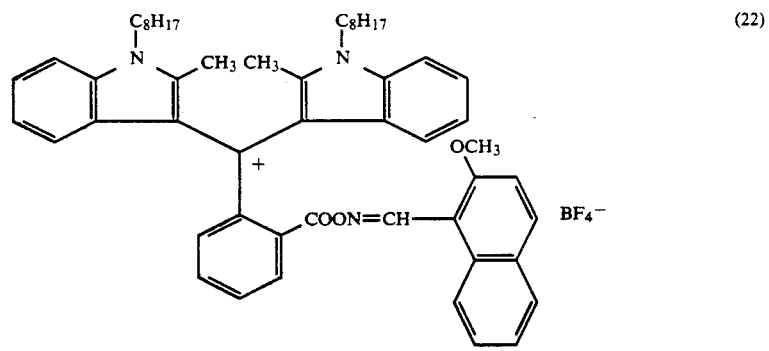
(22)
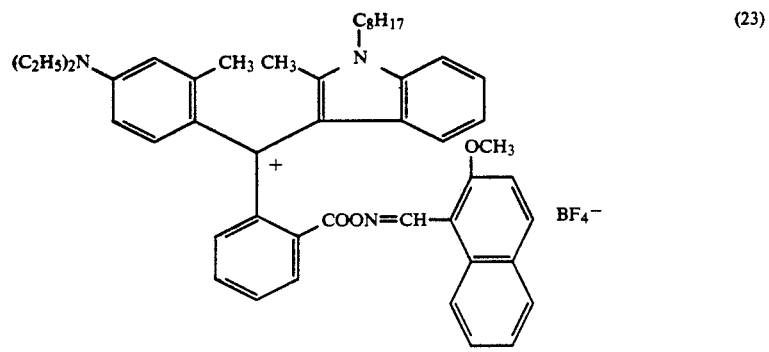
(23)

-continued
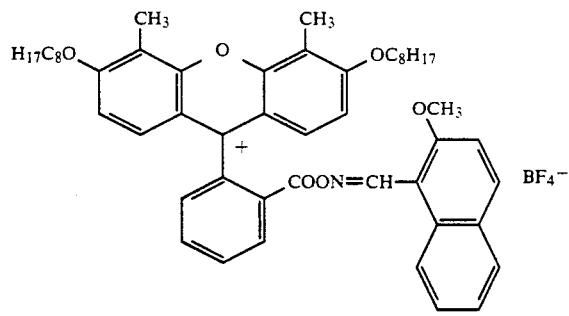
(24)
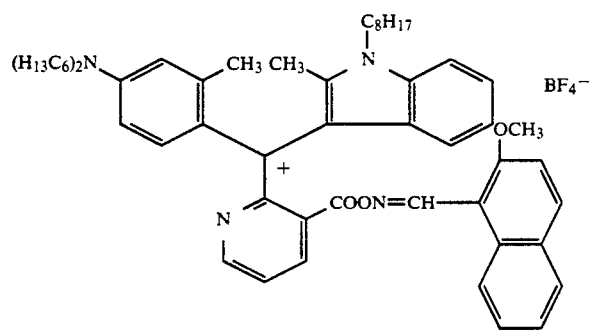
(25)
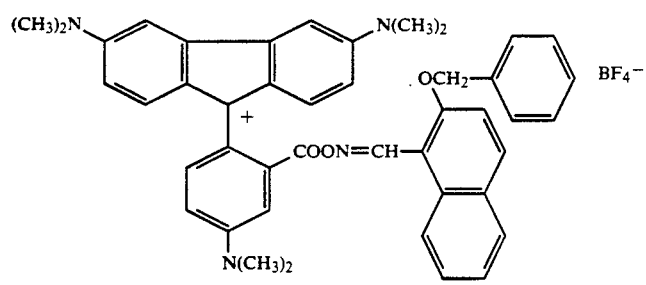
(26)
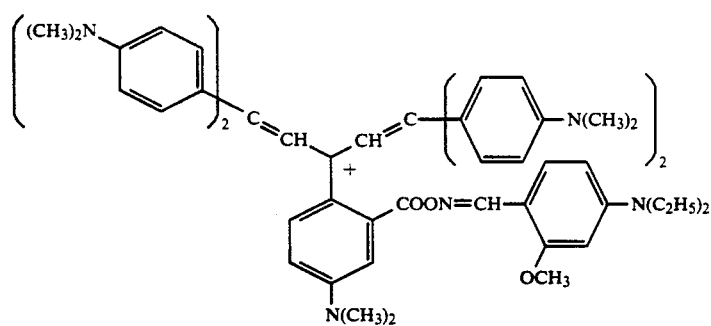
(27)
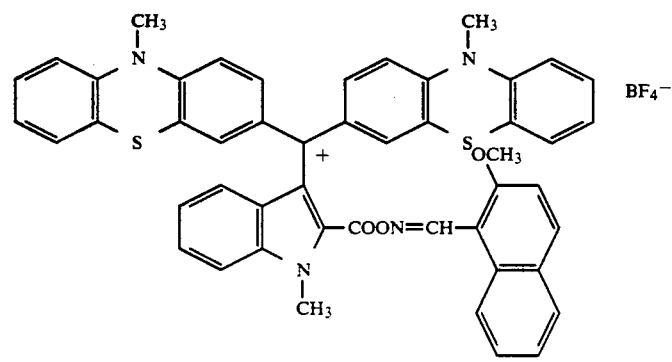
(28)

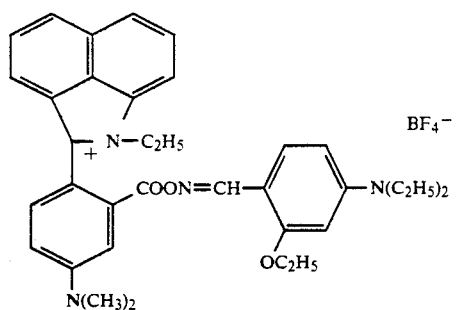
(29)
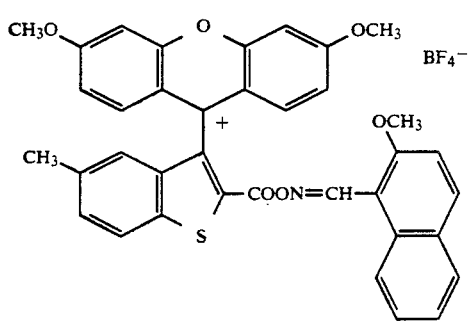
(30)
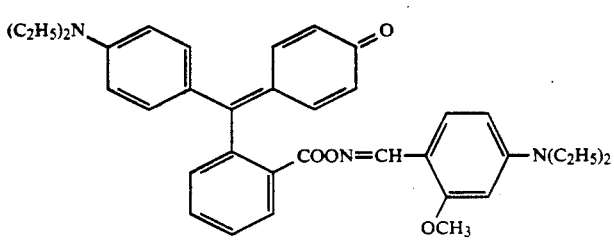
(31)
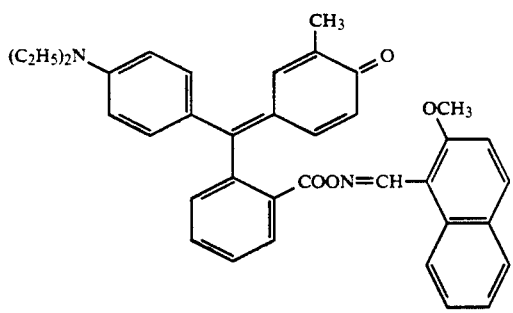
(32)
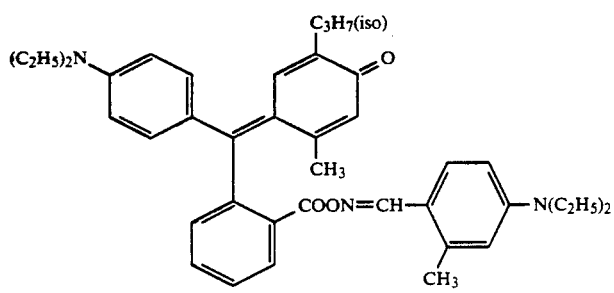
(33)

-continued
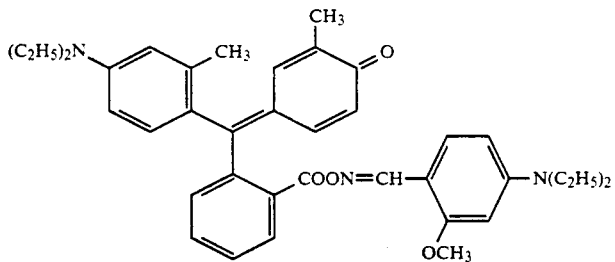 (34)
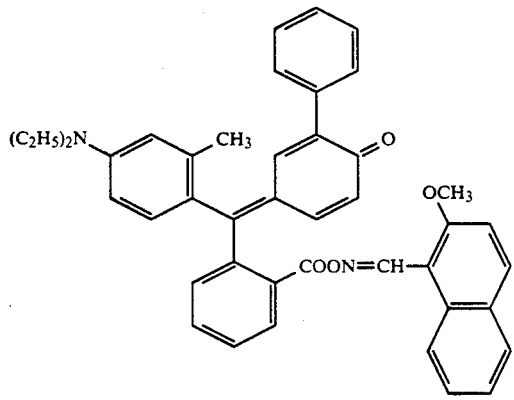 (35)
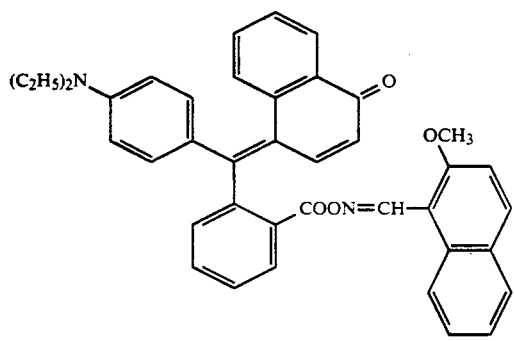 (36)
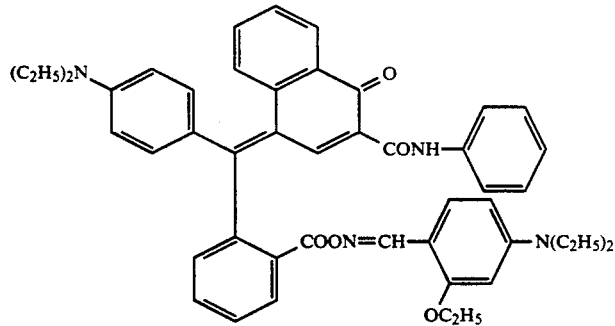 (37)
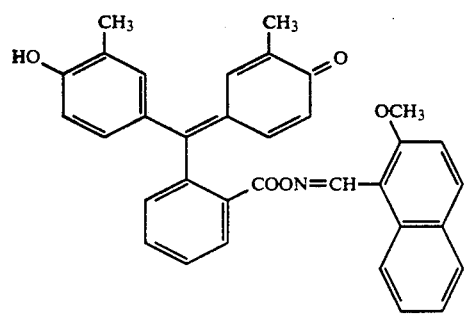 (38)

-continued
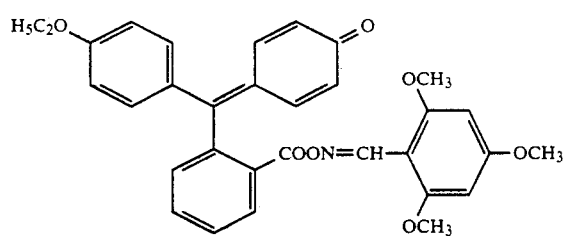 (39)
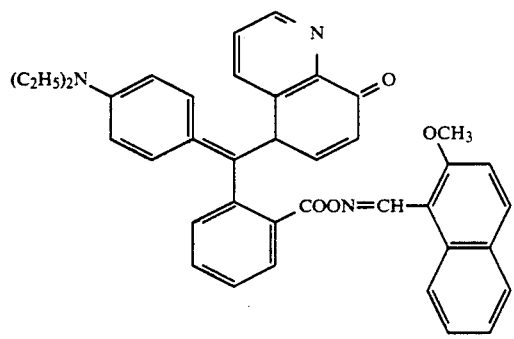 (40)
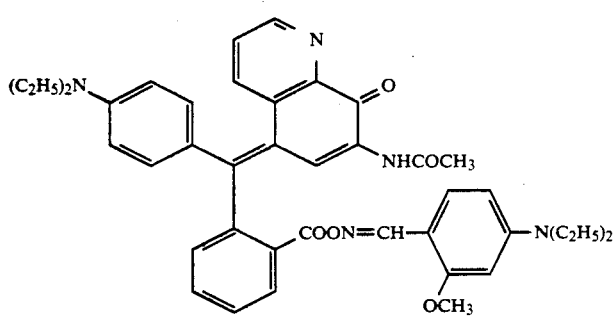 (41)
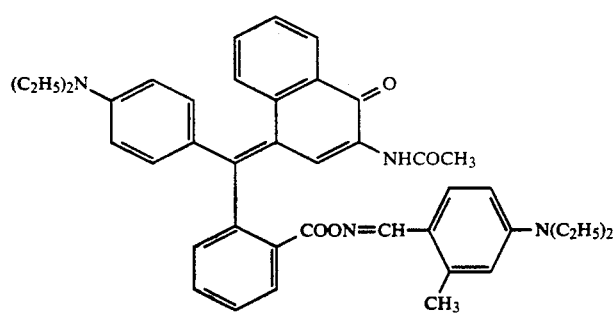 (42)
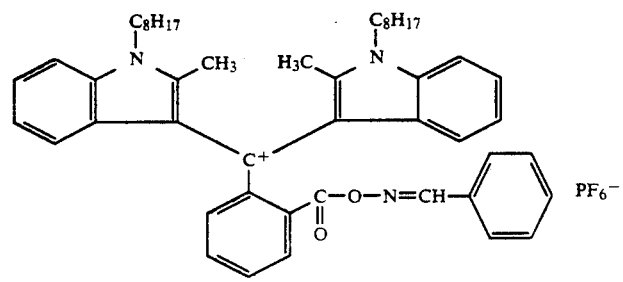 (43)

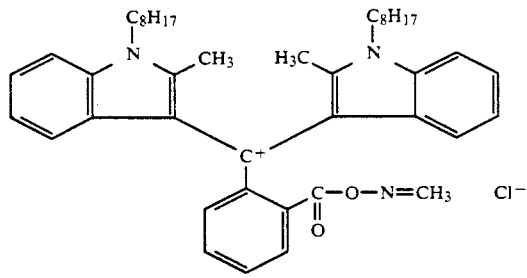
(44)

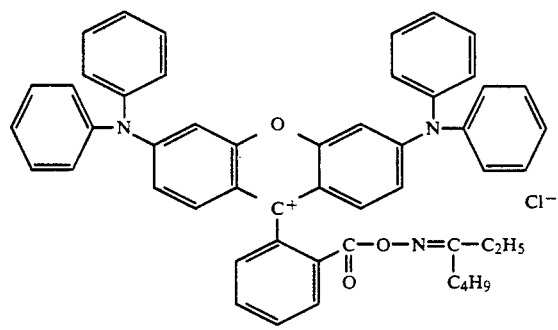
(45)

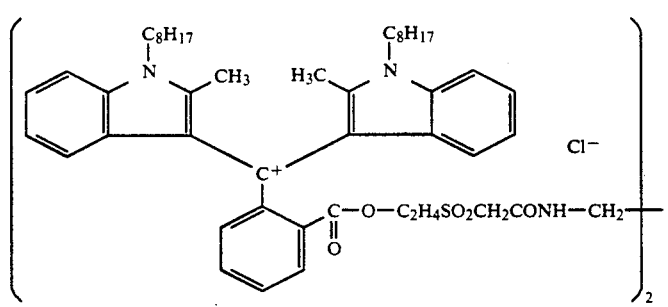
(46)

There are several processes for synthesizing the dyes to be used in the present invention, the most popular process being condensation between a dye carboxylic acid and an aldoxime or an alcohol. The schemes of condensation using an aldoxime or an alcohol are shown below.

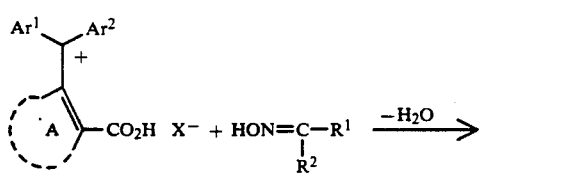

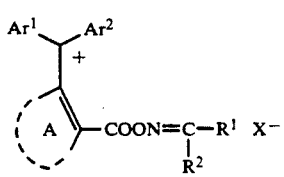

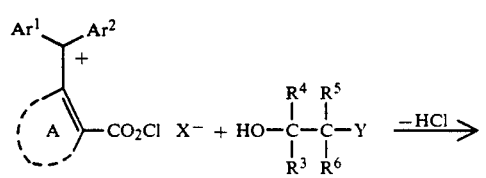

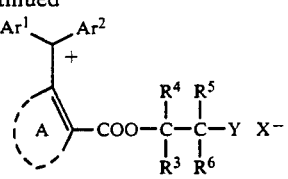

The condensation reaction between the carboxylic acid and the aldoxime or the alcohol is advantageously conducted by converting the carboxylic acid to an acid chloride, an active ester, a mixed acid anhydride or the like to activate it, and reacting the activated derivative with an aldoxime or an alcohol in the presence of a base.

As the ethylenically unsaturated compound to be used in the present invention, there may be used polymerizable compounds having at least one ethylenically unsaturated double bond within the molecule. For example, acrylic acid and salts thereof, acrylic acid esters, and acrylic amides; methacrylic acid and salts thereof methacrylic acid esters and methacrylamides; maleic anhydride and maleic acid esters; itaconic acid and itaconic acid esters; styrenes; vinyl ethers; vinyl esters; N-vinylheterocyclic compounds; aryl ethers; allyl esters; and the like may be used.

Of these, those polymerizable compounds which have a plurality of ethylenically unsaturated double bonds within a molecule are preferable. Examples thereof include acrylic acid esters or methacrylic acid esters of polyhydric alcohols such as trimethylolpropane and pentaerythritol; acrylate- or methacrylate-terminated epoxy resins and acrylate- or methacrylate-terminated polyesters; and the like. Examples of particularly preferable compounds are ethylene glycol diacrylate, ethylene glycol dimethacrylate, trimethylol propane triacrylate, pentaerythritol tetraacrylate, dipentaerythritol hydroxypentaacrylate, hexanediol-1,6-dimethacrylate and diethylene glycol dimethacrylate.

As to the molecular weight of the ethylenically unsaturated compound, a molecular weight of about 100 to about 5,000 is preferable, with about 300 to about 2,000 being more preferable.

The content of the ethylenically unsaturated compound is preferably 10 wt% or more, more preferably 15 wt% or more, most preferably 60 wt% or more, based on the total weight of the photo-polymerizable composition. If the content is less than 10 wt%, the difference in setting degree between exposed portion and unexposed portion is so small that good image quality cannot be obtained.

In the present invention, a combination of a photo-polymerization initiator to be described hereinafter and a spectrally sensitizing dye which loses its color upon being heated is used as a photo-polymerization initiating composition. In the case of selecting an ultraviolet ray region as a wavelength region of light to which the recording material of the present invention responds, the dye which loses its color upon being heated may not be a spectrally sensitizing dye to the ultraviolet ray-responsive photo-polymerization initiator.

As the preferable photo-polymerization initiator to be used in the present invention, those compounds which can initiate photo-polymerization of the aforesaid compounds containing an ethylenically unsaturated bond may be used alone or in a combination of two or more.

Preferable specific examples of the photo-polymerization initiator include the following compounds: aromatic ketones such as benzophenone, 4,4'-bis(dimethylamino)benzophenone, 4-methoxy-4,4'-dimethylaminobenzophenone, 4,4'-dimethoxybenzophenone, 4-dimethylaminobenzophenone, 4-dimethylaminoacetophenone, benzyl, anthraquinone, 2-tert-butylanthraquinone, 2-methylanthraquinone, xanthone, thioxanthone, 2-chlorothioxanthone, 2,4-diethylthioxanthone, fluorenone, acridone, etc.; benzoin and benzoin ethers such as benzoin methyl ether, benzoin ethyl ether, benzoin isopropyl ether, benzoin phenyl ether, etc.; 2,4,5-triarylimidazole dimers such as 2-(o-chlorophenyl)-4,5-diphenylimidazole dimer, 2-(o-chlorophenyl)-4,5-di(m-methoxyphenyl)imidazole dimer, 2-(o-fluorophenyl)-4,5-diphenylimidazole dimer, 2-(o-methoxyphenyl)-4,5-diphenylimidazole dimer, 2-(p-methoxyphenyl)-4,5-diphenylimidazole dimer, etc.; polyhalogen compounds such as tetrachlorocarbon, phenyltribromomethylsulfone phenyl trichloromethyl ketone, etc.; compounds described in JP-A-53-133428 (corresponding to U.S. Pa. No. 4,189,323), JP-B-57-1819 (the term "JP-B" as used herein means an "examined Japanese patent publication") (corresponding to U.S. Pat. No. 3,987,037), JP-B-57-6096 (corresponding to U.S. Pat. No. 4,212,970 and 4,232,106), and U.S. Patent 3,615,455; S-triazine derivatives having a trihalogen-substituted methyl group, described in JP-A-58-29803, such as 2,4,6-tris(trichloromethyl)-S-triazine, 2-methoxy-4,6-bis(trichloromethyl)-S-triazine, 2-amino-4,6-bis(trichloromethyl)-S-triazine, 2-(p-methoxystyryl)-4,6-bis(trichloromethyl)-S-triazine, etc.; organic peroxides described in, for example, JP-A-59-189340, such as methylethylketone peroxide, cyclohexanone peroxide, 3,3,5-trimethylcyclohexanone peroxide, benzoyl peroxide, di-tert-butyl diperoxyisophthalate, 2,5-dimethyl-2,5-di(benzoylperoxy)hexane, tert-butylperoxybenzoate, $\alpha,\alpha'$-bis(tert-butylperoxyisopropyl)benzene, dicumyl peroxide, 3,3',4,4'-tetra-(tert-butyl peroxycarbonyl)benzophenone, etc.; azinium compounds described in, for example, U.S. Pat. No. 4,743,530; organoboran compounds described in, for example, EP 0223587, such as tetramethylammonium salt of triphenylbutylborate, tetrabutylammonium salt of triphenylbutylborate, tetramethylammonium salt of tri(p-methoxyphenyl)butylborate, etc.; diaryliodonium salts; iron-allene complex; and others well known in the art.

In addition, a combination of two or more compounds is also known as a photo-polymerization initiator system and can be used in the present invention. Examples of the combination of two or more compounds include a combination of 2,4,5-triarylimidazole dimer and mercaptobenzoxazole, a combination of 4,4'-bis(dimethylamino)benzophenone and benzophenone or benzoin methyl ether described in U.S. Pat. No. 3,427,161, a combination of benzoyl-n-methylnaphthothiazoline and 2,4-bis(trichloromethyl)-6-(4'-methoxyphenyl)triazole described in U.S. Pat. No. 4,239,850, a combination of dialkylaminobenzoic acid ester and dimethylthioxanthone described in JP-A-57-23602, and a combination of three compounds of 4,4'-bis(dimethylaminobenzophenone, benzophenone, and polyhalogenated methyl compound described in JP A-59-78339 (corresponding to U.S. Pat. No. 4,584,260). As more preferable examples, there are a combination of 4,4'-bis(diethylamino)benzophenone and benzophenone, a combination of 2,4-diethylthioxanthone and ethyl 4-dimethylaminobenzoate, and a combination of 4,4'-bis(-diethylamino)benzophenone and 2,4,5-triarylimidazole dimer.

Of these photo-polymerization initiators, S-triazine derivatives having a trihalogen-substituted methyl group, organic peroxides, azinium salt compounds and organoboran compounds are particularly preferable compounds.

The photo-polymerization initiators are incorporated in an amount of preferably 0.1 to 20 wt%, more preferably 0.2 to 15 wt%, most preferably 5 to 10 wt%, based on the total weight of the photopolymerizable composition. If the amount is less than 0.1 wt%, there is insufficient sensitivity, whereas if more than 20 wt%, no further increase in sensitivity is expected.

In the present invention, a base or a base precursor may properly be used for the purpose of accelerating the color-losing reaction of the dye or spectrally sensitizing dye which loses its color upon being heated. Specific examples of the base include guanidine, triphenylguanidine, tricyclohexylguanidine, piperidine, morpholine, p-toluidine, 2-picoline, etc. Preferred as the base precursor are those which, when heated, undergo some reaction to release a base, such as a salt comprising an organic acid and a base capable of undergoing decarboxylation upon being heated, and a compound capable of releasing an amine by a reaction such as an intramolecular nucleophilic substitution reaction, Lossen rearrangement or Beckmann rearrangement. Specific examples of the base precursor include salts comprising bases such as guanidine, triphenylguanidine, tricyclohexylguanidine, piperidine, morpholine, p-toluidine, 2-picoline, etc. and acids such as acetic acid, trichloroacetic acid, phenylsulfonylacetic acid, 4-methylsulfonylphenylsulfonylacetic acid, 4-acetylaminomethyl propionic acid, oxalic acid, maleic acid, succinic acid, fumaric acid, carbonic acid, bicarbonic acid, etc.

These bases or base precursors may be introduced into the recording material as solid-dispersed particles, or microcapsules to be described hereinafter with or without an oil dissolving it. These bases or base precursors may be incorporated in any position of the recording material, for example, the photo-polymerization initiator composition or a layer different from the layer containing the photo-polymerization initiator composition, as long as they generate a base upon being heated which in turn acts on the spectrally sensitizing dye of the present invention for the dye to lose its color.

The base or base precursor is added to the recording material in an amount of preferably 0 to 100 mols, more preferably 1 to 5 mols, per mol of the spectrally sensitizing dye. If the amount is less than 1 mol, the degree of color disappearance upon heating is insufficient.

Microencapsulation of the base or base precursor may be conducted by known techniques. For example, reference may be made to U.S. Pat. No. 4,743,528, JP-A-61-279593 (corresponding to U.S. Pat. No. 4,686,547), JP-A-59-190886 and 60-6493 (corresponding to U.S. Pat. No. 4,650,740), JP-A-61-279593, etc. The base or base precursor may exist in the microcapsules as a solution or in a solid-dispersed state.

The photo-hardenable composition of the present invention may also be microencapsulated for use. For example, microencapsulation may be conducted by reference to EP 0223578 and the above-mentioned patents. The average size of the microcapsules may be desirably to 20 μm or smaller. In general, a particle adjusted to 20 μm or smaller. In general, a particle size of more than 20 μm is likely to deteriorate the quality of the printed letter. In order to avoid pressure fog, the particle size of microcapsules be preferably adjusted to 8 μm or smaller.

In addition to these compounds, a thermal polymerization inhibitor may, if necessary, be added to the photopolymerizable composition. The thermal polymerization inhibitor is added for the purpose of inhibiting thermal polymerization or polymerization over time of the photopolymerizable composition. Addition of the inhibitor serves to enhance chemical stability of the photopolymerizable composition upon its preparation or storage. Examples of the thermal polymerization inhibitor include p-methoxyphenol, hydroquinone, t-butylcatechol, pyrogallol, 2-hydroxybenzophenone, 4-methoxy-2-hydroxybenzophenone, cuprous chloride, phenothiazine, chloranil, naphthylamine, β-naphthol, 2,6-di-t-butyl-p-cresol, nitrobenzene, dinitrobenzene, picric acid, p-toluidine, etc.

The thermal polymerization inhibitor is added to the polymerizable in an amount of preferably 0.001 to 5 wt%, more preferably 0.01 to 1 wt%, based on the total weight of the photo-polymerizable composition. If the amount is less than 0.001 wt%, thermal stability deteriorates, whereas if more than 5 wt% is used, sensitivity decreases.

For the purpose of dynamically and mechanically strengthening, forming a film and avoiding adhention, a high polymer binder may optionally be added to the photo-polymerizable composition of the present invention. As such a high polymer binder, natural and synthetic high polymer compounds and high polymer latexes known in the art may be used. For example, there are water-soluble high polymers such as gelatin, polyvinyl alcohol, hydroxyethylcellulose, polyvinyl pyrrolidone, casein and starch; solvent-soluble high-polymers such as polystyrene, polyvinyl formal, polyvinyl butyral, acrylic resin (e.g., polymethyl methacrylate, polybutyl acrylate, polymethyl methacrylate, polybutyl methacrylate or a copolymer thereof), phenol resin, styrene-butadiene resin, ethyl cellulose, epoxy resin and urethane resin, or high polymer latexes thereof.

The photo-polymerizable composition of the present invention and the aforesaid various constituents are, if necessary, dissolved in a solvent, coated on a desired support and dried to obtain the recording material of the present invention. Examples of the solvent to be used for dissolving the constituents include water, an alcohol (such as methanol, ethanol, n-propanol, isopropanol, n-butanol, sec-butanol, methylcellosolve, or 1-methoxy-2-propanol), a halogen-containing solvent (such as methylene chloride or ethylene chloride), a ketone (such as acetone, cyclohexanone or methyl ethyl ketone), an ester (such as methyl cellosolve acetate, ethyl acetate or methyl acetate), toluene, xylene, etc. These solvents may be used alone or as a mixture of two or more. To coat the composition on the support, there may be used a blade coater, rod coater, knife coater, roll doctor coater, a comma coater, a reverse roll coater, a transfer roll coater, gravure roll coater, a kiss roll coater, a curtain roll coater, an extrusion coater, etc. The recording layer has a thickness of suitably 0.1 to 50 μ, preferably 0.5 to 10 μ, more preferably 1 to 5 μ.

The recording material of the present invention may be used for various purposes. For example, it may be used for copiers, facsimile machines, printers, labels, color proofs, overhead projectors, second originals, etc. Supports to be suited for these uses include paper, coated paper, laminated paper and synthetic paper, transparent films such as polyethylene terephthalate film, cellulose triacetate film, polyethylene film, polystyrene film and polycarbonate film, plates of metals such as aluminum, zinc and copper, and those materials described above which have been subjected to various treatments such as surface treatment, undercoating treatment, metal vacuum deposition treatment, etc. These supports may have a backing layer such as a sliding layer, antistatic layer, an anticurling layer, an adhesive layer or the like depending upon the end use.

The recording material of the present invention enables one to record with a higher sensitivity using a light in the range of an ultraviolet ray to a light near the infrared region. A wide variety of light sources including a mercury lamp, a xenon lamp, a tungsten lamp, a metal halide lamp, various laser such as argon laser, herium-neon laser or semiconductor laser, LED, a fluorescent lamp, etc., may be employed. Further, a monosheet type recording material can be obtained which can record a distinct, color stain-free image since color of the spectrally sensitizing dye used loses its color.

Specific synthesis examples of dyes to be used in the present invention are described below.

SYNTHESIS EXAMPLE 1 a. 2-Methoxy-1-naphthoaldoxime:

80 g of 2-methoxy-1-naphthoaldehyde, 66 g of sodium acetate and 35.5 g of hydroxylamine hydrochloride were added to a mixture of 400 ml of ethanol and 180 ml of water, and the solution was refluxed for 2 hours. The reaction solution was poured into 1 liter of water and, after it was allowed to stand for 3 hours at room temperature, crystals formed and were collected by filtration to obtain 85 g of 2-methoxy 1-naphthoaldoxime.

b. Sodium salt of 2-methoxy-1 naphthoaldoxime:

7.1 g of 2 methoxy-1-naphthoaldoxime was added to 300 ml of dry acetonitrile, and 1.7 g of a 50% oily sodium hydride was gradually added thereto, followed by stirring the mixture at room temperature for 30 minutes until generation of hydrogen stopped.

c. Compound (6):

12.6 g of 3,3-bis(4-dimethylaminophenyl)-6-dimethylaminophthalide was added to 100 ml of dry methylene chloride, then 4.45 g of oxalyl chloride was dropwise added thereto at 0 to −5° C. After being stirred at 0° C for 1 hour, the solution was added to the above-described solution of sodium salt of 2-methoxy-1-naphthoaldoxime at 0° to −5° C., followed by stirring at room temperature for one hour.

After completion of the reaction, the reaction solution was concentrated under reduced pressure. Then, 10 ml of ethanol and 20 ml of a 40% aqueous solution of tetrafluoroboric acid were added thereto, and a blue precipitate of formed compound (6) was collected by filtration and washed with a small amount of water and ether. Yield: 4.5 g; decomposition point: above 250° C.

SYNTHESIS EXAMPLE 2 a. Compound (22):

18.7 g of 3,3-bis[(1 octyl-2-methyl)indol-3-yl]-phthalide was added to 100 ml of dry methylene chloride, then 4.45 g of oxalyl chloride was dropwise added thereto at 0° to 5° C. After being stirred at 0° C. for 1 hour, the solution was added to the above-described solution of sodium salt of 2-methoxy-1-naphthoaldoxime at 0° to −5° C., followed by stirring at room temperature for one hour.

After completion of the reaction, the reaction solution was concentrated under reduced pressure. Then, 10 ml of ethanol and 20 ml of a 40% aqueous solution of tetrafluoroboric acid were added thereto, and a red precipitate of formed compound (22) was collected by filtration and washed with a small amount of water and ether. Yield: 6.7 g; decomposition point: above 250° C.

The present invention is now illustrated in greater detail by reference to the following examples which, however, are not to be construed as limiting the present invention in any way.

EXAMPLE 1

0.24 g of a dye of compound example (22) which loses its color upon being heated and 0.11 g of a photopolymerization initiator of tetramethylammonium triphenylbutylborate were dissolved in 5 ml of methanol. To this solution was added 30 g of an ethylenically unsaturated compound of trimethylolpropane triacrylate. This solution was added to a mixed solution of 23 g of a 4% gelatin aqueous solution and 6 g of a 10% solution of sodium dodecylbenzenesulfonate, and the resulting mixture was emulsified for 2 minutes at 4000 r.p.m. in a homogenizer (made by Nippon Seiki K.K.). This emulsion was coated on a woodfree paper (60 g/m2) in a dry weight of 3 g/m2 of the coated layer using a coating bar, and then dried at 30° C. for 10 minutes to obtain a light and heat-sensitive recording material.

The thus obtained light- and heat sensitive recording material was exposed through a stepwedge (Fuji Step Guide P; made by Fuji Photo Film Co., Ltd.) and a 550-nm interference filter (model MIF; made by Nippon Sinku Kogaku K.K.) using a 500 W xenon lamp. Thereafter, it was heated on a 140° C. hot plate for 20 seconds. Thus, the dye in unset portion lost its color, leaving a magenta-color, distinct image of the dye in photoset portions.

EXAMPLE 2

A light and heat-sensitive recording material was obtained in the same manner as in Example 1 except for using 0.4 g of IRGACURE 651 (product of CIBA-GEIGY) in place of 0.11 g of tetramethylammonium triphenylbutylborate used in Example 1 as the photopolymerization initiator.

The thus obtained light- and heat-sensitive recording material was exposed through a stepwedge by ultraviolet light emitted from a 1000-W high-pressure mercury lamp (jet light made by ORC MANUFACTURING Co., Ltd.). Then, it was heated on a 140° C. hot plate for 20 seconds. Thus, the dye in the unset portion lost its color, leaving a magenta-color, distinct image of the dye in photoset portions.

EXAMPLE 3

When the light- and heat-sensitive recording material obtained in Example 1 was subjected to thermal head letter-printing using OKIFAX 8500R (made by OKI Electric Industry Co., Ltd.), the color in the heated portions disappeared, leaving a magenta-color image of the dye in the non-heated portions. When this image was exposed to ultraviolet light emitted from a 1000-W high-pressure mercury lamp (jet light made by ORC MANUFACTURING Co., Ltd.), the remaining monomer in the recording material was polymerized, thereby fixing the image.

EXAMPLE 4

0.18 g of a dye of compound example (6) which loses its color upon being heated and 0.11 g of a photopolymerization initiator of tetramethylammonium triphenylbutylborate were dissolved in 5 ml of methanol. To this solution was added 15 g of an ethylenically unsaturated compound of trimethylolpropane triacrylate to prepare a solution, and 0.2 g of a fine powder of a base precursor of tricyclohexylguanidine carbonate was added thereto and was well dispersed therein. Then, 15 g of a 33% solution of polymethyl methacrylate in acetone was added thereto as a binder, and the mixture was well stirred to prepare a coating solution. This coating solution was coated on a woodfree paper (60 g/m$^2$) in a dry weight of 3 g/m$^2$ of the coated layer using a coating bar, and then dried at 30° C. for 20 minutes. An aqueous solution of polyvinyl alcohol was coated thereon as an oxygen barrier layer in a dry weight of 3 g/m$^2$ of the coated layer, then dried at 30° C. for 20 minutes to obtain a light- and heat-sensitive recording material.

The thus obtained light- and heat-sensitive recording material was exposed through a stepwedge to ultraviolet light emitted from a 1000-W high pressure mercury lamp (jet light made by ORC MANUFACTURING Co., Ltd.). Heating the material by a 150° C. hot plate for 20 seconds gave a blue distinct image.

COMPARATIVE EXAMPLE 1

A recording material was obtained in the same manner as in Example 1 except that 0.2 g of a spectrally sensitizing dye of bis[(1-octyl-2-methyl)indol-3-yl]-2-(methoxycarbonyl)phenylcarbenium perchlorate was used in place of the dye used in Example 1.

The thus obtained light- and heat sensitive recording material was exposed through a stepwedge (Fuji Step Guide P; made by Fuji Photo Film Co., Ltd.) and a 550-nm interference filter (model MIF; made by Nippon Sinku Kogaku K.K.) using a 500 W xenon lamp. Thereafter, it was heated on a 140° C. hot plate for 20 seconds. However, the dye did not lose its color, and the material appeared wholly magenta, failing to form an image.

EXAMPLE 5

A light- and heat-sensitive recording material was obtained in the same manner as in Example 4 except that 0.3 g of a dye of compound example (46) was used in place of 0.18 g of a dye of compound example (6) used in Example 4 as the spectrally sensitizing dye.

The thus obtained light- and heat-sensitive recording material was exposed and heated in the same manner as in Example 4. A magenta-color distinct image was obtained.

While the present invention has been described in detail and with reference to specific embodiments thereof, it is apparent to one skilled in the art that various changes and modifications can be made therein without departing from the spirit and scope of the present invention.

What is claimed is:

1. A light- and heat-sensitive composition which contains a photo-hardenable composition containing a photo-hardenable compound and a photoinitiator, and at least one dye selected from the group represented by the following general formulae (I), (II), (III) and (IV):

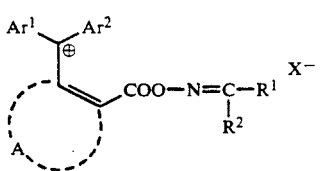
(I)

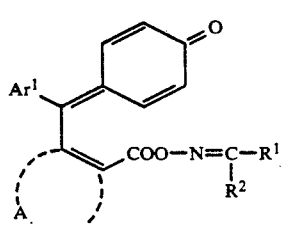
(II)

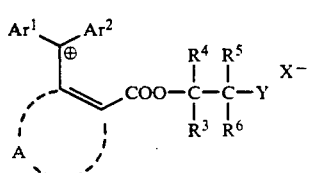
(III)

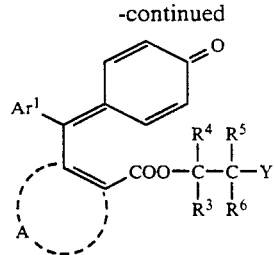
(IV)

wherein $Ar^1$ and $Ar^2$ each represents an aryl group or a heteroaryl group and may be bound to each other to form a ring; $Rs^{1-6}$ each represents a hydrogen atom, an alkyl group, an alkenyl group, an aralkyl group, an aryl group or a heteroaryl group, provided that both $R^1$ and $R^2$ are not hydrogen atoms at the same time; Y represents CN, $NO_2$, $SO_2$—$R^7$, SO—$R^7$, COO—$R^7$ or

in which $R^7$ and $R^8$ is each a hydrogen atom, an alkyl group, an alkenyl group, an aralkyl group, an aryl group or a heteroaryl group; A represents atoms necessary for forming a 5- or 6-membered ring; $X^-$ represents a residue having an electric charge of −1, with the ring

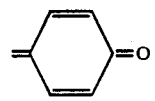

in the general formulae (II) and (IV) being optionally fused with an aromatic ring or a heterocyclic ring, and $Ar^1$, $Ar^2$, $R^1$, $R^2$, ring A and ring

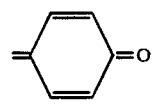

being optionally substituted by other substituents.

2. The light- and heat-sensitive composition as set forth in claim 1, wherein said dye is a spectrally sensitizing dye to a photo-polymerization initiator in said photo-hardenable composition.

3. The light- and heat-sensitive composition as set forth in claim 1, wherein the dye is represented by general formula (I).

4. The light- and heat-sensitive composition as set forth in claim 1, wherein the dye is represented by general formula (II).

5. The light- and heat-sensitive composition as set forth in claim 1, wherein the dye is represented by general formula (III).

6. The light and heat-sensitive composition as set forth in claim 1, wherein the dye is represented by general formula (IV).

7. A light- and heat-sensitive recording material, which contains a support having said light- and heat-sensitive composition as set forth in claim 1 provided on at least one side thereof.

8. The light- and heat-sensitive composition as set forth in claim 1, wherein the photo-hardenable composition is selected from the group consisting of a photopolymerizable composition, a composition containing a photo-crosslinkable resin, and a mixture thereof.

9. The light- and heat-sensitive composition as set forth in claim 8, wherein the photo-hardenable composition is a photopolymerizable composition comprising an ethylenically unsaturated compound and a photopolymerization initiator.

10. A light- and heat-sensitive recording material, which contains a support having said light- and heat-sensitive composition as set forth in claim 8 provided on at least one side thereof.

11. A light- and heat-sensitive recording material, which contains a support having said light- and heat-sensitive composition as set forth in claim 9 provided on at least one side thereof.

* * * * *